United States Patent [19]
Smith et al.

[11] Patent Number: 5,997,513
[45] Date of Patent: *Dec. 7, 1999

[54] SYRINGE COVER COOPERATING WITH NEEDLE COVER

[76] Inventors: Jerry A. Smith, 6020 Bayou Rd., Mobile, Ala. 36605; Joseph M. Gerlecz, 1138 W. 26th St., Lynn Haven, Fla. 32444

[*] Notice: This patent issued on a continued prosecution application filed under 37 CFR 1.53(d), and is subject to the twenty year patent term provisions of 35 U.S.C. 154(a)(2).

[21] Appl. No.: 08/668,866

[22] Filed: Jun. 24, 1996

Related U.S. Application Data

[60] Provisional application No. 60/007,453, Nov. 22, 1995.

[51] Int. Cl.$^6$ ........................................ A61M 5/32
[52] U.S. Cl. .................... 604/198; 604/110; 604/187; 604/263; 128/919
[58] Field of Search ........................ 604/110, 181, 604/187, 192, 195, 197, 198, 263, 240–243; 128/919

[56] References Cited

U.S. PATENT DOCUMENTS

| | | | |
|---|---|---|---|
| 4,062,353 | 12/1977 | Foster et al. | 128/1.1 |
| 4,365,626 | 12/1982 | House | 128/218 |
| 4,702,738 | 10/1987 | Spencer | 604/198 |
| 5,366,447 | 11/1994 | Gurley | 604/192 |
| 5,403,288 | 4/1995 | Stanners | 604/232 |
| 5,558,649 | 9/1996 | Shields | 604/192 |
| 5,562,624 | 10/1996 | Righi et al. | 604/110 |

*Primary Examiner*—Wynn Wood Coggins
*Assistant Examiner*—Deborah Blyveis

[57] ABSTRACT

An improvement on a syringe needle protection device and system for practicing the same is shown utilizing a hollow needle cover, or simply cover, which may slide over or within a syringe cylinder. The invention envisions having a needle cap which protects a needle. The hollow needle cover has a reduced end capable of receiving and holding or ejecting the needle cap. The device may also include a means for releasable locking onto the needle cap so that the needle cap locks onto the needle cover. When the cap is being replaced the needle cap can be snapped onto the needle cover until the cap is released when the cap is fixed back in place over the needle. Typically the cap will snap into place onto the needle holder. A locking mechanisms is envisioned which locks the needle cap to the needle cover. This mechanism can prevent the needle cap from being removed from the needle cover until the needle cover is fully extended over the needle. The cover allows the needle holder to be unscrewed or broken off when the user is finished with the needle.

14 Claims, 12 Drawing Sheets

Fig. 11

SYRINGE COVER COOPERATING WITH NEEDLE COVER

PRIORITY

This patent claims priority based on the provisional filing serial number: 60/007,453 filed Nov. 22, 1995.

BACKGROUND OF THE INVENTION

Prior Art

The prior art shows several variations on the theme of self-shielding or automatic shielding hypodermic syringes. These patents generally can be spoken of as directed to providing a cover or shield which prevents someone from sticking themselves with the needle.

These needle covers generally describe similar elements. A syringe, a needle (with a means for attaching the needle to the syringe), and a mechanism for providing a temporary cover for the needle. In these particulars, the present invention is similar to the prior art.

The invention differs from the prior art at the point where the needle cap, that part of the needle assembly which protects the needle when it is shipped from a manufacturer, interacts with the needle cover which covers the exposed needle on the syringe.

In reviewing the what is believed to be the closest prior art, U.S. Pat. No. 4,911,693 (Paris) discloses a hypodermic syringe needle guard with a first cylindrically shaped part surrounds and is fixed to the needle base which is mounted on the forward end of the syringe body. A second cylindrical part is mounted within the first part for axial movement between a forward position where the needle is surrounded for protection of the needle prior to mounting and between injections and a position in which the needle is exposed during an injection. A spring urges the second part towards the forward position. Locking elements are provided for permanently locking the second part in a third, axially spaced position to protect the needle after it has been discarded. Prior to and between injections, the second part may be non-permanently locked in the forward position by rotating it relative to the first part.

U.S. Pat. No. 5,137,521 (Wilkins) discloses a safety shield slidable mounted upon a disposable hypodermic syringe and needle assembly and having an elongated guide slot which cooperates with a resilient tab cooperating therewith to maintain orientation between the syringe body and the telescoping shield. A resilient locking tab integral with the syringe body cooperates with a pair of spaced slots arranged along the telescoping shield to define the initial shielded position and the usable position respectively. The telescoping shield to define the initial shielded position ad the usable position respectively. The telescoping shield includes a shoulder which receives the bent-over flexible tab to lock the shield in the shielded position to prevent contact with the needle, facilitating safe handling of the assembly.

U.S. Pat. No. 5,318,547 (Altschuler) discloses a sheathed syringe assembly including a syringe having a cylindrical body provided with a needle at one thereof and a plunger slidable disposed within said cylindrical body for aspirating or dispensing substances into or from the cylindrical body. A sheath assembly comprised of inner and outer tubular members is attached to the cylindrical body. The inner tubular member is telescopically received in the outer member for reciprocal movement therein between a retracted position exposing said needle and an extended position covering said needle to prevent accidental needle stick.

U.S. Pat. No. 4,892,521 (Laico, et al.) discloses a protective cover for a hypodermic needle which employs a pair of guide rods for guiding a protective cap from a retracted position to an extended protective position for shielding the hypodermic needle. A guide member projects transversely from the needle base and forms a pair of apertures which receive and interact with the guide rods. The guide rods are fixed to a protective cap portion of the cover. A guide rod mechanism is also employed in connection with a retractable, foldable sheath embodiment. The protective cover assembly may also take form of telescopic shield sections which lock in the extended protective position by means of a cooperative projection/groove locking engagement.

U.S. Pat. No. 5,222,945 (Basnight) discloses a safety syringe which includes a barrel having an interior chamber for containing fluid, and a needle mounted at one end of the barrel. The needle has a bore in fluid communication with the interior chamber in the barrel. A plunger is slidable mounted within the interior chamber of the barrel for displacing fluid within the barrel through the needle to administer fluid to a patient. A protective shield is slidable mounted on the barrel and is moveable between an extended position in which the needle is concealed and a retracted position in which the needle is exposed. The protective shield is moveable between first, second and third position. In the first position, the protective shield is extended over the needle and is releasibly locked to protect the needle prior to use. In the second position, the protective shield is retracted and is releasibly locked to facilitate use of the syringe. In the third position, the protective shield is again extended to cover the needle and is irreversibly locked to prevent reuse of the syringe. Reuse of the syringe is further prevented by a plunger locking mechanism which is engaged when the plunger is fully depressed.

GENERAL DISCUSSION OF THE INVENTION

The present invention is directed towards an improvement over the prior art hypodermic syringe with needle protection devices. The process and product disclosed in more detail below is most useful where the user desires a reusable and sterilized hypodermic syringe using disposable needles and carpules requiring periodic recovering of the needle tip to prevent injury. It is also useful where the needle is to be disposed of separately from the syringe.

The invention differs from the prior art at the point where the needle cap, that part of the needle assembly which protects the needle when it is shipped from a manufacturer, interacts with the needle cover which covers the exposed needle on the syringe.

Several mechanisms are disclosed to have the cover releasably hold the needle cap.

It is therefore an object of this invention to provide a hypodermic cover capable of removing a needle cover and then receiving the needle cover and replacing it onto the needle holder upon completion of using the needle.

It is a further object of the invention to provide for a hypodermic cover for the purpose set forth previously which cannot release the needle cover or receive the needle cover until the hypodermic cover completely shields the needle cover.

It is a further object of the invention to provide a needle holder, needle cover, and hypodermic cover which cooperates together in order to allow the needle cover to be selectively removed or replaced onto the needle cover by way of the hypodermic cover.

These and other objects and improvements of the invention will be better understood from a reading of the following detailed description with reference to the attached drawings on which like numerals designate the parts described.

BRIEF DESCRIPTION OF THE DRAWINGS

Drawings

FIG. 5a and b shows a needle cap and the needle cap in conjunction with an automated cap grasping and releasing mechanism, respectively.

FIGS. 9a–f shows several different adjustments of a hypodermic syringe embodying the invention and shows the process from the attachment of the needle to the removal of the needle cap using the process embodied herein.

FIG. 10 shows the invention of FIG. 6 defining a semi-circular opening for removal of the needle holder and needle cap.

FIGS. 10a, b, and c show the opening of FIG. 6 in a detail view, a closed squared cover and the same squared cover in the open position respectively.

DETAILED DISCUSSION OF THE PREFERRED EMBODIMENT(S)

Figure 1:
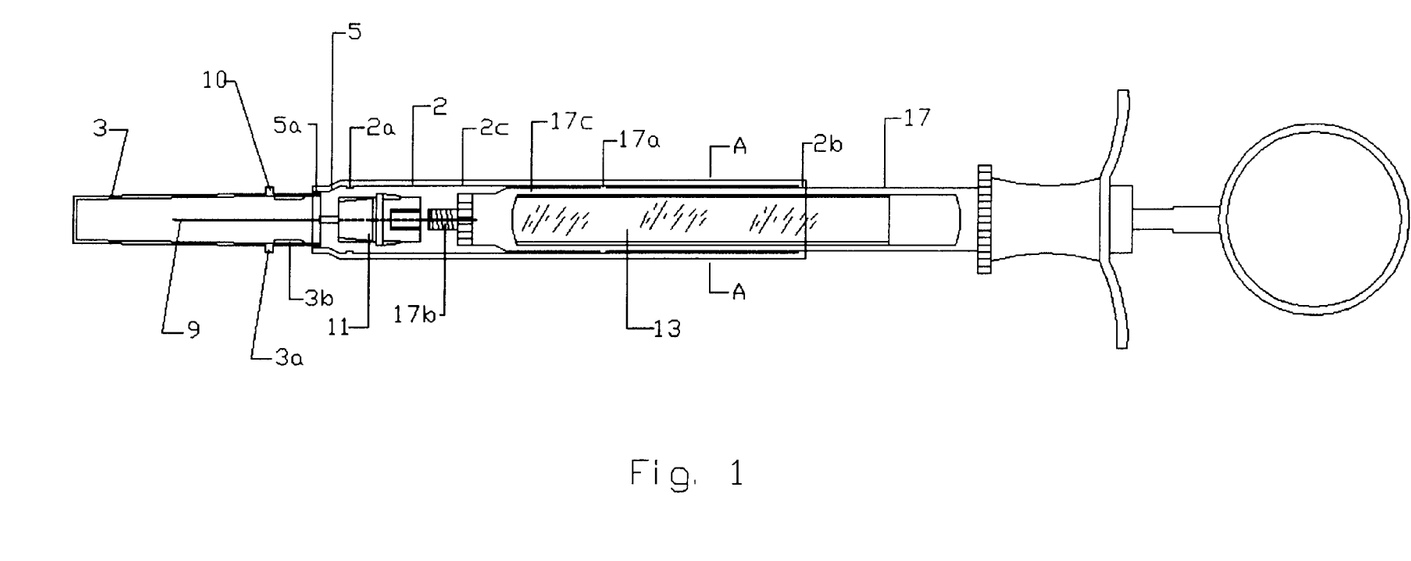
FIG. 1 shows a longitudinal cross section of the preferred embodiment of the invention.

As can best be seen by reference to FIG. 1, the invention comprises an improvement on a syringe needle protection device and a system for practicing the same. The embodiment shown utilizes a hollow needle cover 2 which may slide over (or within in alternate embodiments) a syringe cylinder 17.

When fully assembled, the invention comprises a needle cap 3 which protects a needle 9. The needle cap 3 is provided with a frictional surface 18. This frictional surface 18 may be gripped by a gripping surface 19 on the cover 2. As can be seen, the arrangement can be reversed without changing the inventive concept embodied herein by providing a frictional surface on an interior portion of cap 3 into which a gripping surface of cover 19 can slide.

FIG. 1 shows the invention comprises a needle cap 3 which has a raised ridge 3a which is in accordance with the design one would find in the art.

Figure 4:
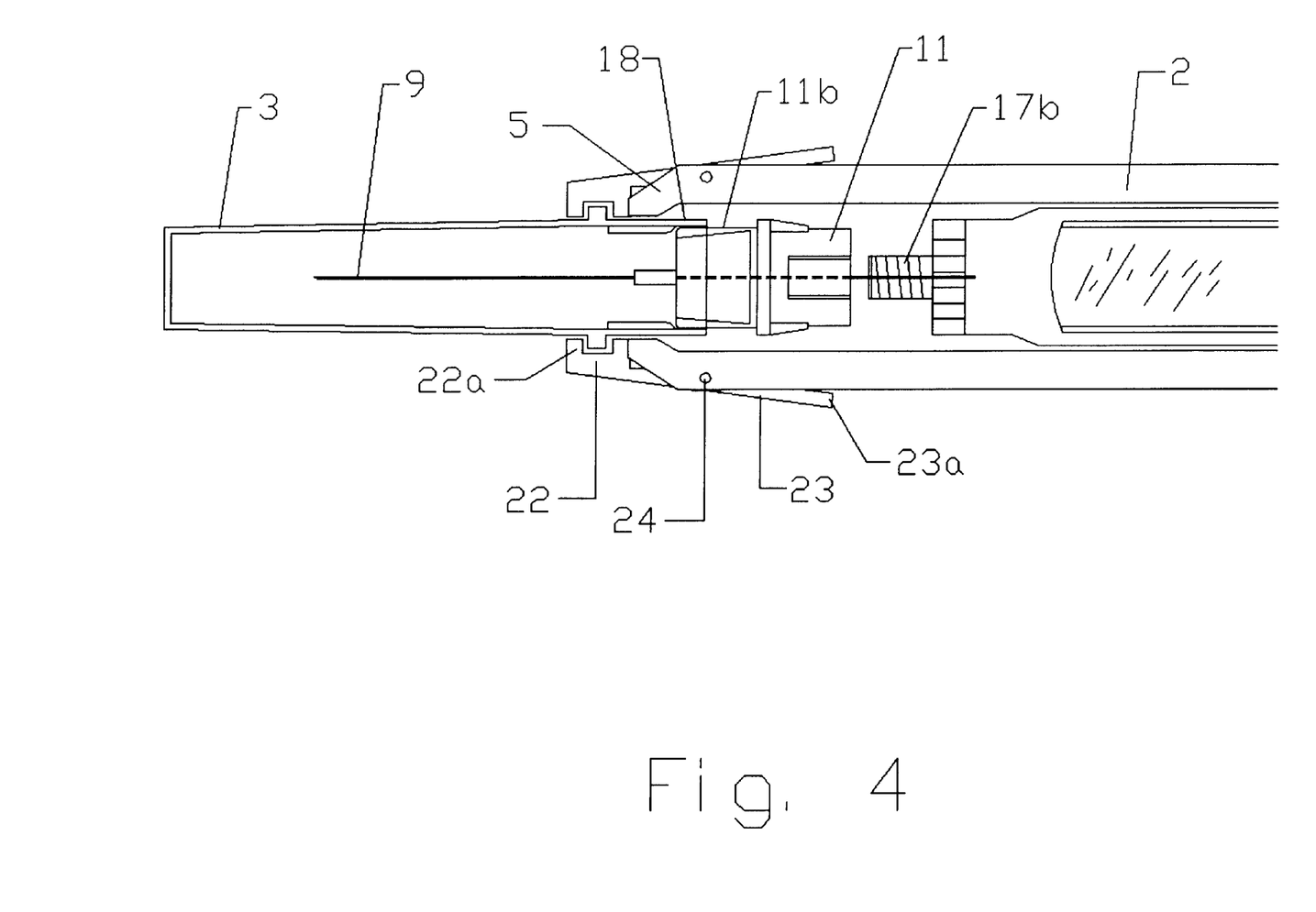
FIG. 4 is a cross-sectional view detail view of the cap grasping mechanism shown in FIG. 3.

The needle cap 3 fits on to a needle holder 11 as shown in FIG. 4 which is also designed and known in the art to hold needle 9.

The inside of the needle cap 3 has ridges 3b which contact the squared walls 11b of the needle holder 11. In this way, when the user turns the cap, the squared walls 11(b) contact the ridges 3b and the needle holder is turned. The turning screws the needle holder 11 onto threads 17b on the syringe cylinder 17 in a manner known in the art.

It is also known in the art that the back of the needle holder 11 has a plastic capable of forming threads to cooperate with the threads 17b of the syringe cylinder 17.

In the preferred embodiment shown in FIG. 1 the invention comprises a needle cover 2 which slides over the hypodermic syringe 17. In the preferred embodiment this cover 2 has a front internal ridge 2a and a rear internal ridge 2b which serves to maintain the cover 2 within the desired area of the hypodermic syringe cylinder 17 which also has an external ridge 17a which serves to block the movement of the cover 2 past the desired point forward or back past the point marked by the location of ridge 17a.

Ridges 2a and 2b on the front and back respectively of the inner circumference of cover 2 prevent the cover from moving past the desired location. In the preferred embodiment, the length of the cover 2 is minimized so that it may be pulled as far from the needle 9 as possible so as not to interfere with the needle.

In this embodiment the ridges 2a, 2b and 17a may cooperate magnetically so that the syringe locks in place when the syringe is moved forward or back the desired distance.

The cover 2 should be able to turn in order to allow for the rear portion of the needle holder 11 to be screwed onto the threads 17b provided on the front of the syringe cylinder 17.

The front of the needle cover 2 has a reduced end 5 which supporting the frictional surface 19. It should be noted that failing to reduce the end 5 and instead having the frictional surface contact the needle cap 3 otherwise would not depart from the inventive concept embodied herein, but would only depart from the preferred embodiment. Similarly, replacement of the frictional surface 19 with a latch mechanism 22 does not depart from the inventive concept embodied herein given these several embodiments.

Figure 2A:
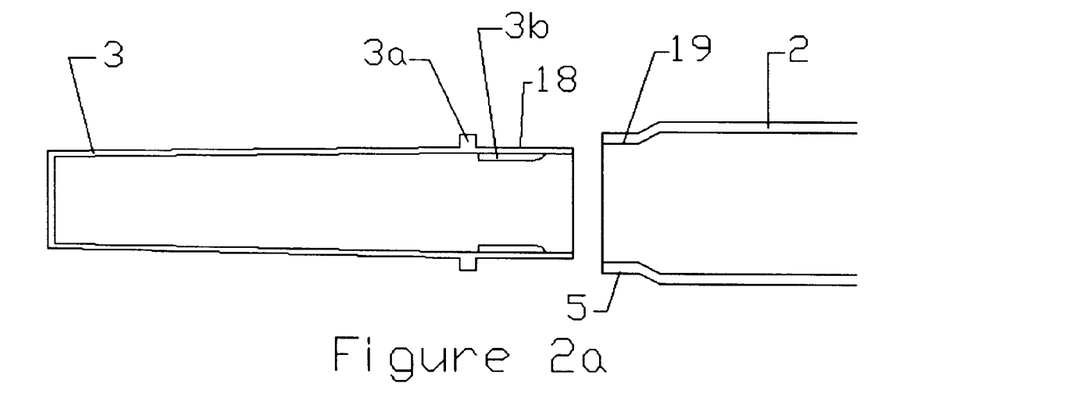
FIGS. 2a, b and c show cross section detail views of three separate joining structures at the point where the needle cap 3 joins the needle cover 5.
Figure 2B:
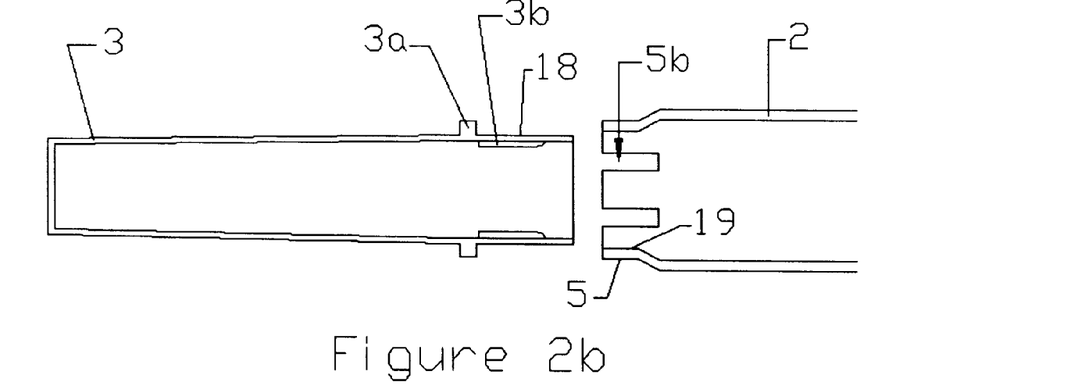
Figure 2C:
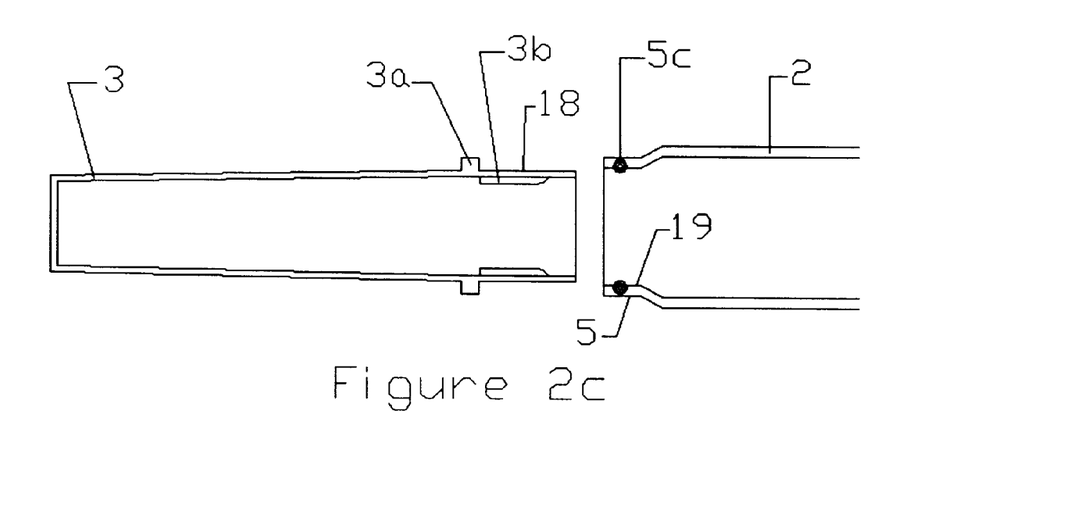

As shown in FIG. 2, this reduced end 5 will interact with the outer circumference of the needle cap 3 in one of several different methods described in more detail below so as to releasably secure the needle cover to the needle cap.

In the preferred embodiment, the needle is typically attached with the cap 3 in place so that the invention need only be fully retracted. However, the cover 2 may slide fully forward until the inner ridge 2b intersects with the outer ridge 17a and snap together by virtue of the magnetic or mechanical action. At this point the needle cap 3 may be inserted securely onto the front 5 of cover 2 so that the inner circumference of 5 is in frictional contact with the outer circumference 3b of the needle cap 3 behind the ridge 3a on the needle cap. The ridge 3a may serve to prevent the needle cap from moving too far within the reduced end 5 of cover 2 forward at this point.

After the user has pulled the cover 2 forward, the frictional surface 18 is held by cover 2. Cover 2 then slides back so that ridge 36 engages needle holder 11 so that the cap and needle may be removed as a sealed unit, thereby reducing the possibility of sticking. The method embodied herein is the method of maintaining the cover in a direction away from the needle and at the point when the cap is engaged to disengage thereby reducing the possibility of an unwanted stick.

In some circumstances it may be required that a greater gripping action be provided than the frictional contact between the internal circumference 5a (gripping surface or means 19) of the reduced end 5 of the cover 2 and the outer circumference 3b (frictional surface 18) of the needle cap 3.

In order to accomplish this result, several alternate embodiments are envisioned which may have a mechanical or magnetic mechanism for increasing the amount of contact between the inner circumference of the cap and the reduced end of the needle cover 5.

One method of accomplishing that is to have the cap raised edge 3a have a magnetic contact with the reduced end 5 of the cover. This method is not preferred because of the problems associated with the magnetic material in this setting. FIG. 2, discussed above shows methods of changing the reduced end 5 to increase the frictional contact.

FIG. 2A shows the reduced end 5 having a gripping surface 19 contacting a frictional surface 18 on the outer surface of the needle cap 3. The cover 2 slides all the way up to the raised edge 3a and sufficient frictional contact between the surfaces 18 and 19 occurs in order to have the parts gripped. This gripping is enhanced if the inner diameter of the cover 2 is substantially or approximately the same size as the outer diameter of the cap 3 so that the cover must flex open or the cap flux inward to make a tight fit.

In order to improve the fit, the end 5 of the cover 2 may define at least one split or gap 5b to allow it to elastically expand to more tightly grip the outer circumference 3b by allowing some expansion between the splits 5b. FIG. 2B shows how this gripping may be augmented by having the cover reduced end define gaps 5b which allow for expansion of the cover reduced end 5 as it slides over the cap 3.

FIG. 2c shows yet another modification where the cover further comprises an internal o-ring seal 5c. This provides an internal o-ring 5c which may be used in order to provide a better frictional surface for gripping the outer circumference 3b of the needle cap 3. In addition, this o-ring seal 5c may be approximately the same size as the area between the cover 2 and the syringe 1 so that as the cover 2 is slid back exposing the needle 9, the o-ring 5c prevents air and moisture from entering the space between the cover and the syringe to prevent the cover from fogging up. This distance between the cover 2 and the syringe 1 may be maintained by one or more longitudinal ridges 28 running the longitudinal length of the internal surface of the cover 2 as can be seen from a cross section of the needle cover and syringe barrel in FIG. 11.

Figure 11:
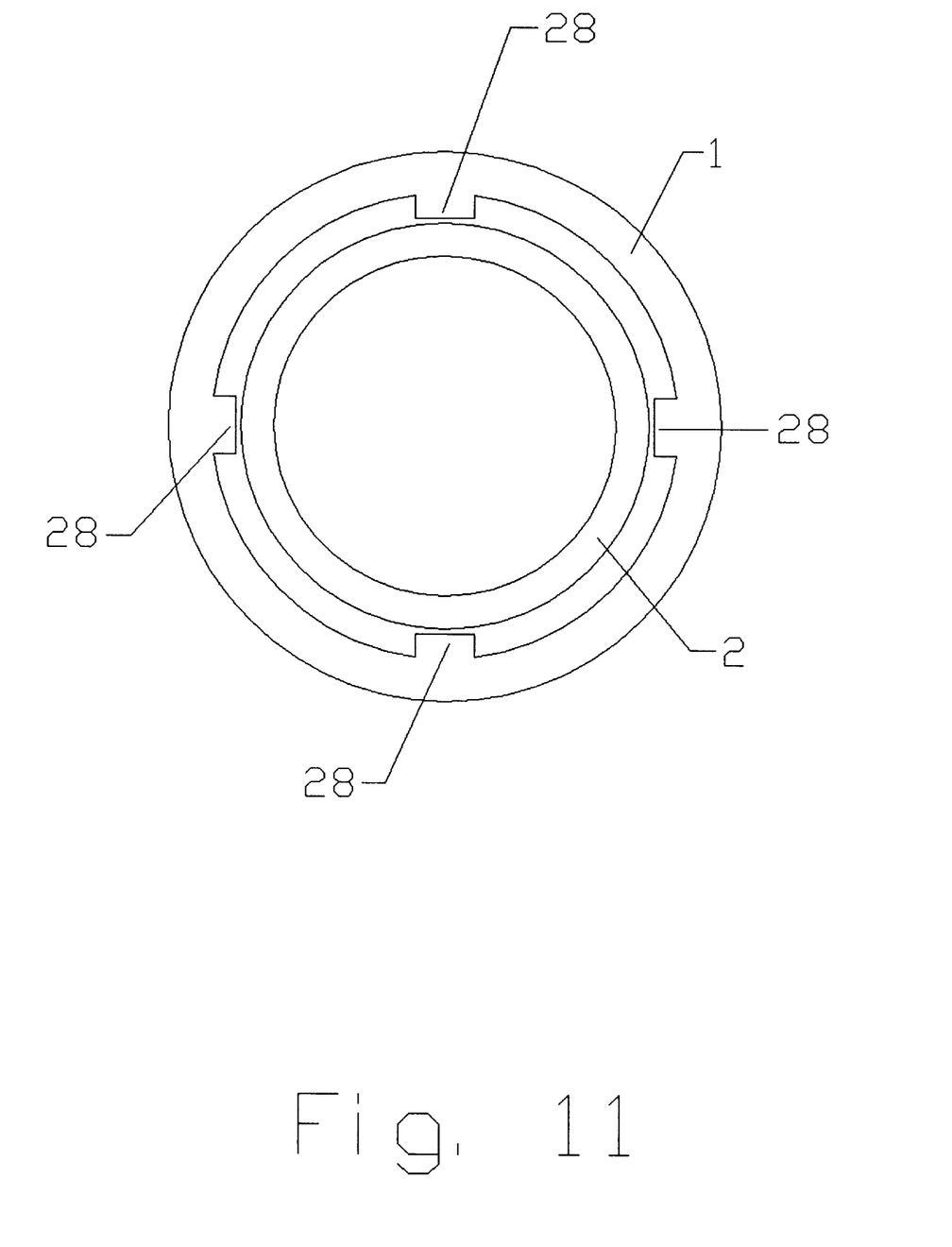
FIG. 11 is a cross sectional view of the embodiment of FIG. 1 through the a—a axis.

In the preferred embodiment, the cover 2 is clear so that the user may look within the cover for various reasons (such as observing the carpule held within the syringe). Two modifications improve this function. First, the connection between the cover and the syringe is made air tight by way of a washer or o-ring seal 40 placed between the syringe and the cover, thus preventing air, such as from the breath of a person's mouth in a dental syringe, from entering the area between the cover and the syringe. Another feature present are nobs or ridges 28 traveling length of the cover 2 which serve to hold the rest of the cover 2 above the syringe 1 to prevent scratching. In this way, only the nobs 28 receive wear, protecting the rest of the cover and preventing it from becoming scratched and opaque.

After the needle 9 and needle holder 11 is fixed onto the syringe cylinder 17 at screw 17b, the needle cover and needle holder and needle cap assembly is moved back towards the threaded end of the syringe cylinder 17 by the user.

As it is slid back the rounded end of the needle holder 11 is guided into the thread 17b on the end of the syringe cylinder 17 allowing the needle holder 11 to be screwed in place and allowing the needle 9 to puncture a carpule (not shown) held in the syringe 17.

After it is screwed in place, the assembly comprised of the needle 9 and the needle holder is disengaged from the needle cap 3 by sliding the cover cylinder 2 forward. The cover cylinder 2 contacts the cap 3 at the cover cylinder's reduced end 5 and pushes the cap 3 off of the needle holder 11. As the cover 2 is moved by sliding forward it removes the needle cover 3 with it.

In the embodiment shown in FIG. 1, the cover cylinder 2 could be designed so as to be broken in half so that it may be removed completely at this point in time or it may be provided so that it can slide completely off the front of the syringe at this point in time by providing a cooperating gap (not shown) between ridge 17a and the ridge 2b which allows the ridge 2b to fit through the ridge 17a to allow the cover 2 to be completely removed.

Since the needle 9 is covered by the cap 3 when it is initially applied, the cover 2 need not be used when attaching the needle. When the needle cap 3 is to be replaced after removal, the cover is slid forward on the syringe over the needle 9 and then the needle cap 3 may be attached to the cover reduced end 5. Then the combination of the cap 3 and cover 2 can be slid backwards on the syringe until the cap 3 is back in place on the needle holder.

When the syringe is not in use the needle 9 can be covered with the cover 2. In the preferred embodiment this is how the syringe functions. When the user is finished using the syringe, the cover 2 is slid filly over the needle until ridge 2b interacts (magnetically) with ridge 17a to fix the cover 2 firmly over the needle 9. The cover 2 may be slit back out of the way at which point ridge 2a interacts (magnetically) with ridge 17a to fully expose the needle 9 and keep the cover 2 out of the way.

To replace the cap, the user holds the cover 2 extended over the needle 9 and snaps the cap 3 back in place on the cover 2. The entire assembly comprising the cap 3 and the cover 2 is then slid back in place in order to fit the cap firmly over the needle holder 11 at which point the needle holder 11 may be unscrewed and removed. As shown in FIG. 10, an opening 25 may be provided in the cover 2. The needle holder may be broken free from the syringe screw 17b by bending the cap 3 and holder towards this opening until the needle holder breaks free.

Figure 10A:
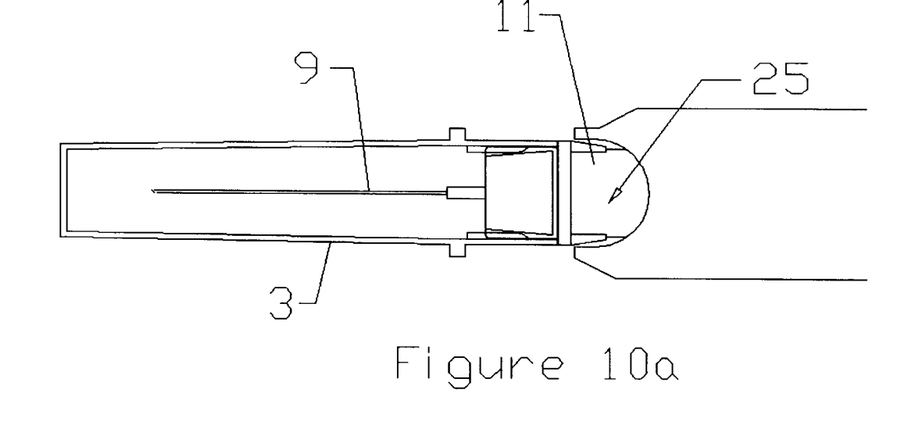
Figure 10B:
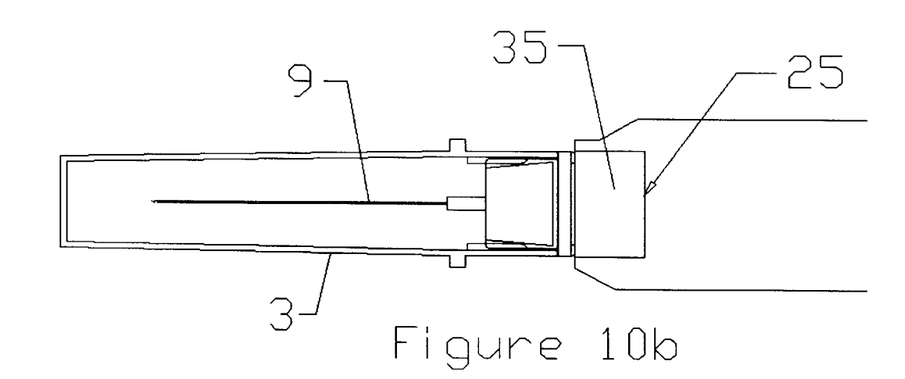

FIG. 10(a) shows a detail of the curved opening 25. FIG. 10(b) shows a modification of this design showing a closed opening, closed by a door 35 which may open to display the opening 25 so that the needle holder 11 may be broken off.

Figure 3:
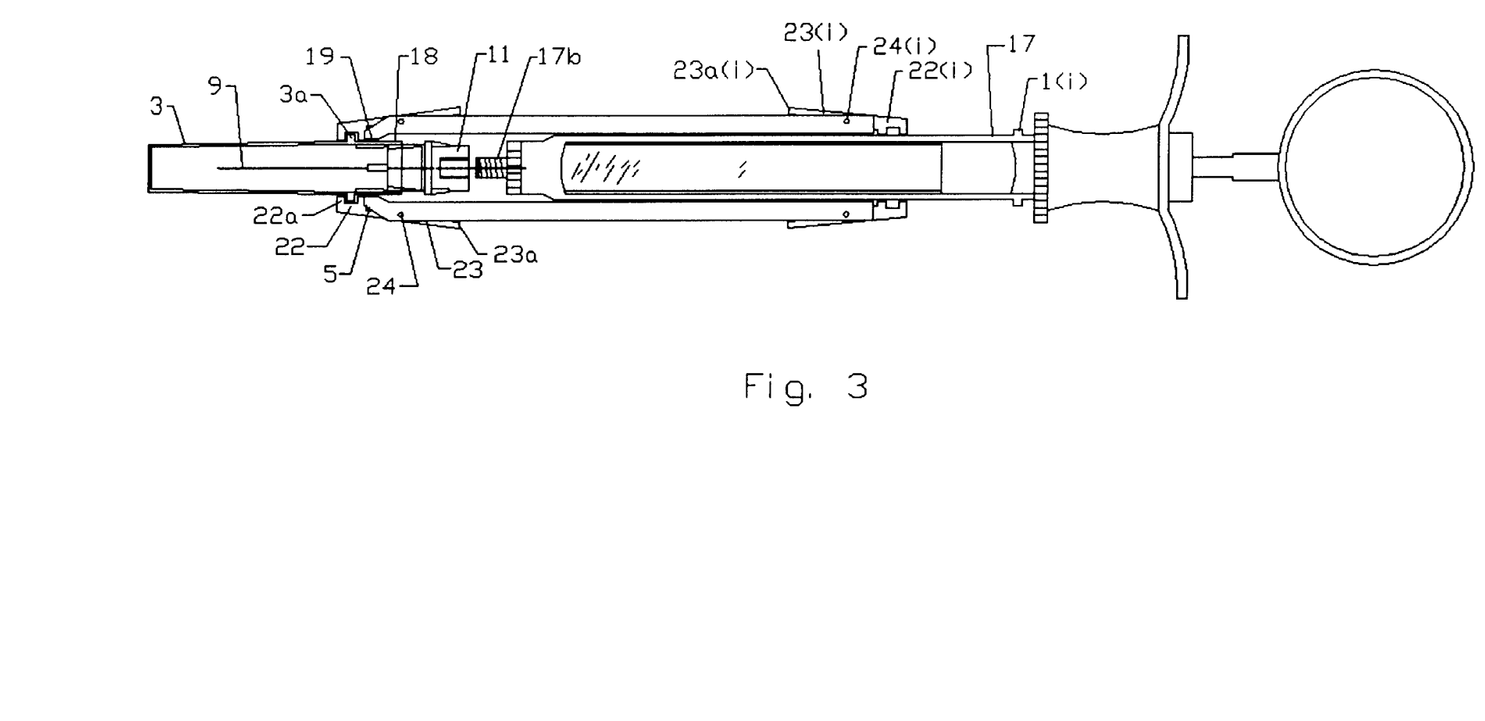
FIG. 3 is a second alternate embodiment of the invention showing a cap grasping mechanism for holding the needle cap and showing a retraction grasping mechanis for holding the cover in the retracted position.

In another embodiment, shown in FIG. 3 a locking mechanism which may have a hand release or a pressure release may be present in order to secure the cover 2 in the desired position. FIG. 3 shows latch mechanisms 22 attached by a pivot 24 to cover 2. An identical, rearwardly located latch 22(i) having a pivot 24(i) latching onto a raised portion of the syringe 1(i) serves to secure the cover 1 back in this embodiment. A slight modification of this embodiment would provide that the gripping mechanism be formed as a part of the manufacture of the reduced end 5 of the cover 2. A gripping means is defined by female member 22 on one end of lever 23 held by way of a pivot, 24 which would be a portion of a plastic forming the lever and gripping mechanism and attaching that to the cover 2.

The user by pressing the rear end 23a of lever 23 lifts the female member 22 so that it may be put in place over the ridge 3a of the cap 3 or removed from the ridge 3a.

Similarly, the rear end 23(a)(i) of the lever 23(i) may be pressed to disengage the rear female member 22(i) from the ridge 1(i).

The design of the female member 22 and ridge of the cap 3 may be altered in several different fashions so as to further secure this relationship. Likewise the location of the female and male members may be reversed in a manner obvious to anyone viewing the invention in order to accomplish this same result.

This mechanism is shown in more detail in FIG. 4 which is a detail view of the embodiment of FIG. 3 showing the latch mechanism 22.

Figure 5A:
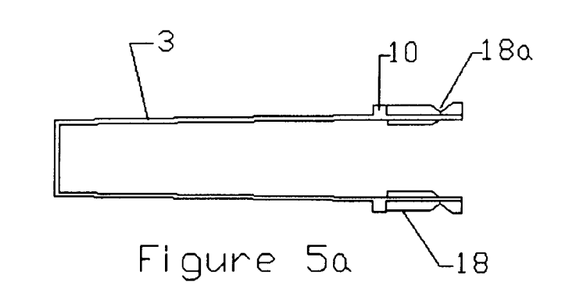
Figure 5B:
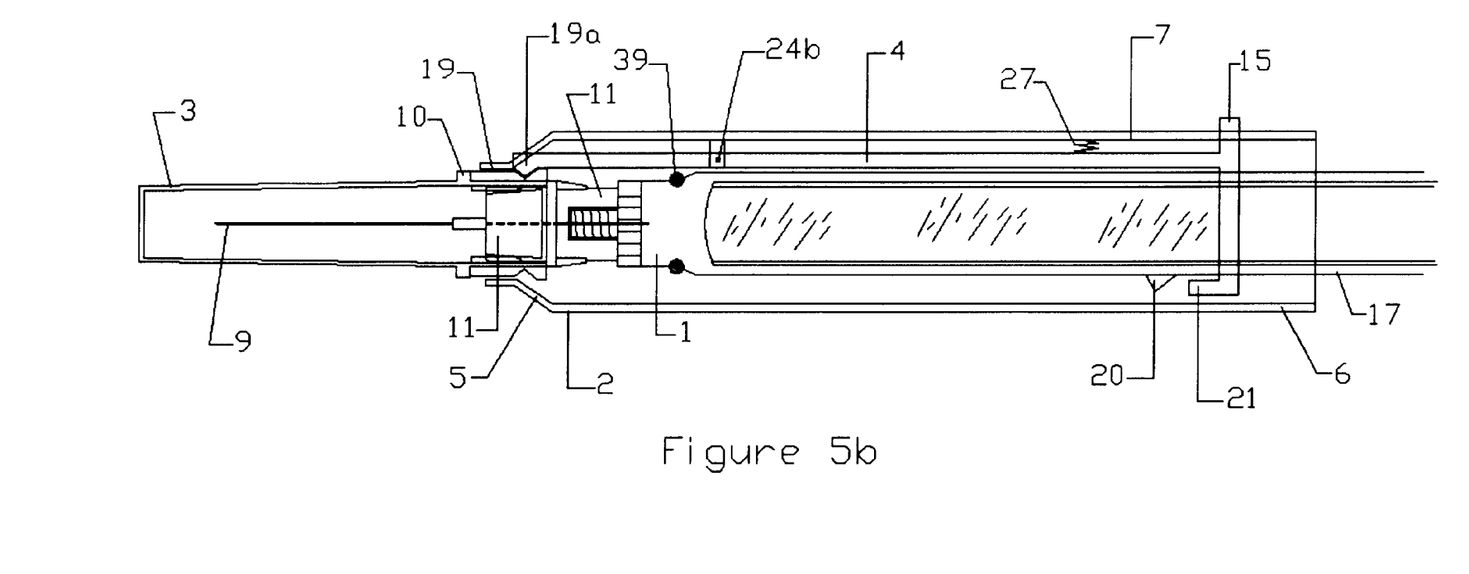

FIG. 5B shows an alternative design having an automated latch mechanism with a manual release 15. As shown in FIG. 5a, a notch 18a is provided in the cap. FIG. 5b shows how this allows for a male extension 19a to fit within the notch 18a as opposed to the female latch 22a shown in FIG. 4. These are merely two different alternatives for the same basic concept.

As shown in the cross section of FIG. 5b, the curved or angled surface 18a receives the angled extension 19a. The connection between 18a and 19a may pop loose as the two are separated.

In the embodiment shown in FIG. 5, an arm 4 which may be a part of the molded plastic cover pivots around a pivot point 24b. The arm 4 ends with the extension 19a which fits into the notch 18a provided in the friction surface 18 of cap 3. In this way the cover 2 need not have a reduced end but may have the same diameter throughout. As shown in FIG. 5 the contact between surface 18 and 19 is still present.

As can be seen by reference to FIG. 5, the invention may have a manual release 15 or an automatic release mechanism which in this case is shown with the interaction of ridge 21 on the cover 2 and ridge 20 on the syringe cylinder.

The same interlocking ridge mechanism may be used in place of the magnetic ridge described in reference to FIG. 1 in order to hold the cover fully extended and fully retracted between the two ridges described in FIG. 1 for the cover and the one ridge on the syringe. The pivot and the mechanism for the spring as shown in FIGS. 5 may be varied if the only purpose is to lock the cover in place along the length of the syringe as shown in FIGS. 6–10 as described in more detail below.

In the embodiment shown in FIG. 5 the pivot mechanism may have additional bias provided by way of a spring 27 in order to hold it in place.

The purpose of this would be to allow the housing to be held more firmly in place on the syringe when the housing is pushed forward pushing off the cap which otherwise covers the needle.

The hollow needle cover has a reduced end capable of receiving and holding or ejecting the needle cover. The device may also include an engaging means for releasable locking onto the needle cap so that the needle cap locks onto the needle cover. In addition, when the cap is being replaced the needle cap can be snapped onto the needle cover until the cap is released when the cap is in place over the needle. Typically the cap may snap into place onto the needle holder. Locking mechanisms such as those described above are envisioned. The first is the cap lock which locks the needle cap to the needle cover. The second is the cover lock 14 to lock the cover over the needle until a release 15 is pressed. These locks may prevent the needle cover from being removed or put into place until the needle cover is in the desired position. For example, this mechanism can prevent the needle cap from being removed from the needle cover until the needle cover is fully extended over the needle.

In order to address this the invention which is used in conjunction with a standard design for a reusable syringe comprises a cylindrical needle cover similar to those found in the prior art. Like the prior art, the cylindrical cover for this particular invention has a reduced end. The improvement in the invention comprises a modification of this reduced end which allows it to removably receive the needle cover. In order to better understand the invention it should be understood that when using reusable syringes you will typically have a carpule of material to be injected by the needles. The hypodermic syringe has a mounting to receive a needle holder which allows the needle holder to puncture the carpule and allow the puncture carpule to communicate with the needle itself. The needle holder has a cover which protects the needle. In order to maintain safety the present invention provides that whenever the needle cover is removed the cylindrical cover is moving towards the working end of the needle so that the possibility of being accidentally stuck due to a failure of the device is reduced as is well described in the art. What is not described in the art is the method in which the needle cover and the cylindrical cover cooperate together to become a single unit as the cylindrical cover moves over the needle removing the needle cover.

In the embodiments shown in FIGS. 2a–2c the needle cover cannot be removed without expending force. FIGS. 4 and 5 replace the use of force on the cap with a release mechanism operating manually or when an automatic release (FIG. 5) operates when the cover extends completely over the needle. However, in the broadest embodiment, it is envisioned that the needle cap and cylindrical cover need only become a single unit as the cap is removed. The added benefit for this type of reusable hypodermic syringe is more particularly seen when the needle cover is replaced on the needle after the user is finished with the specific needle mounting.

Figure 6A:
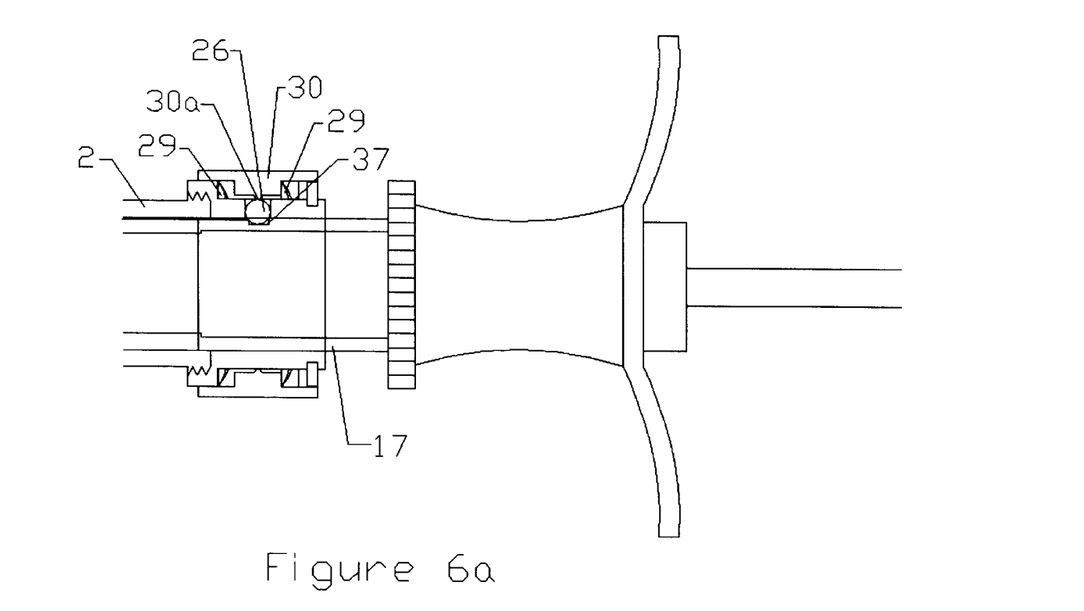
FIGS. 6a and 6b show a second alternate embodiment of the invention detailing a mechanism for selectively locking the cover in place along the external barrel of the syringe.
Figure 6B:
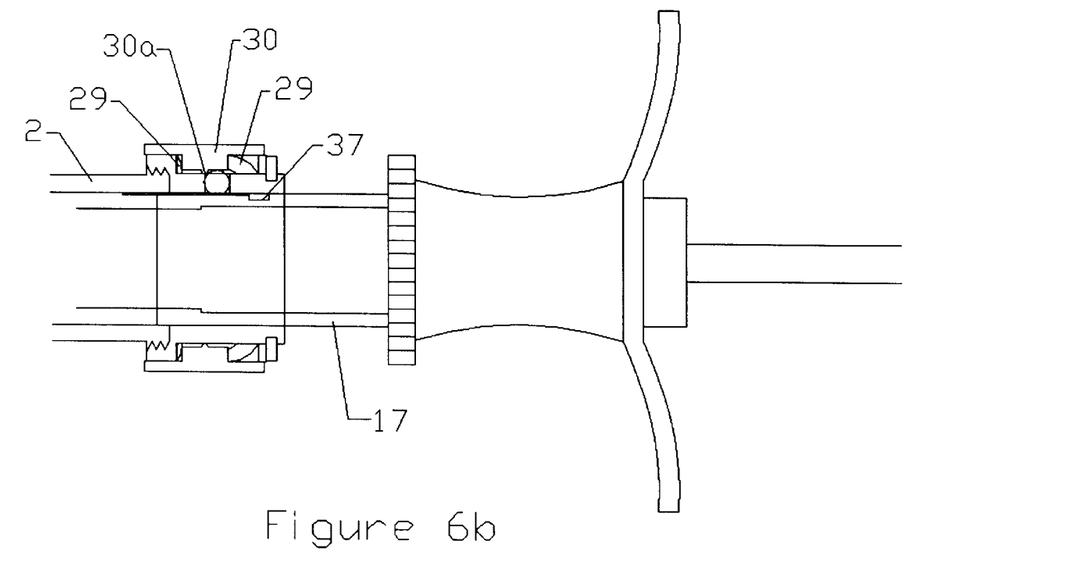

FIGS. 6a and 6b show yet another mechanism for controlling the location of the cover 2 relative to the syringe 1. FIG. 6a shows where a ball 26 fits within a dip or groove 37 in the syringe 1. There may be a front dip 37a and a rear dip 37b to hold the cover 2 forward over the needle 9 or retracted away from the needle 9.

Figure 8:
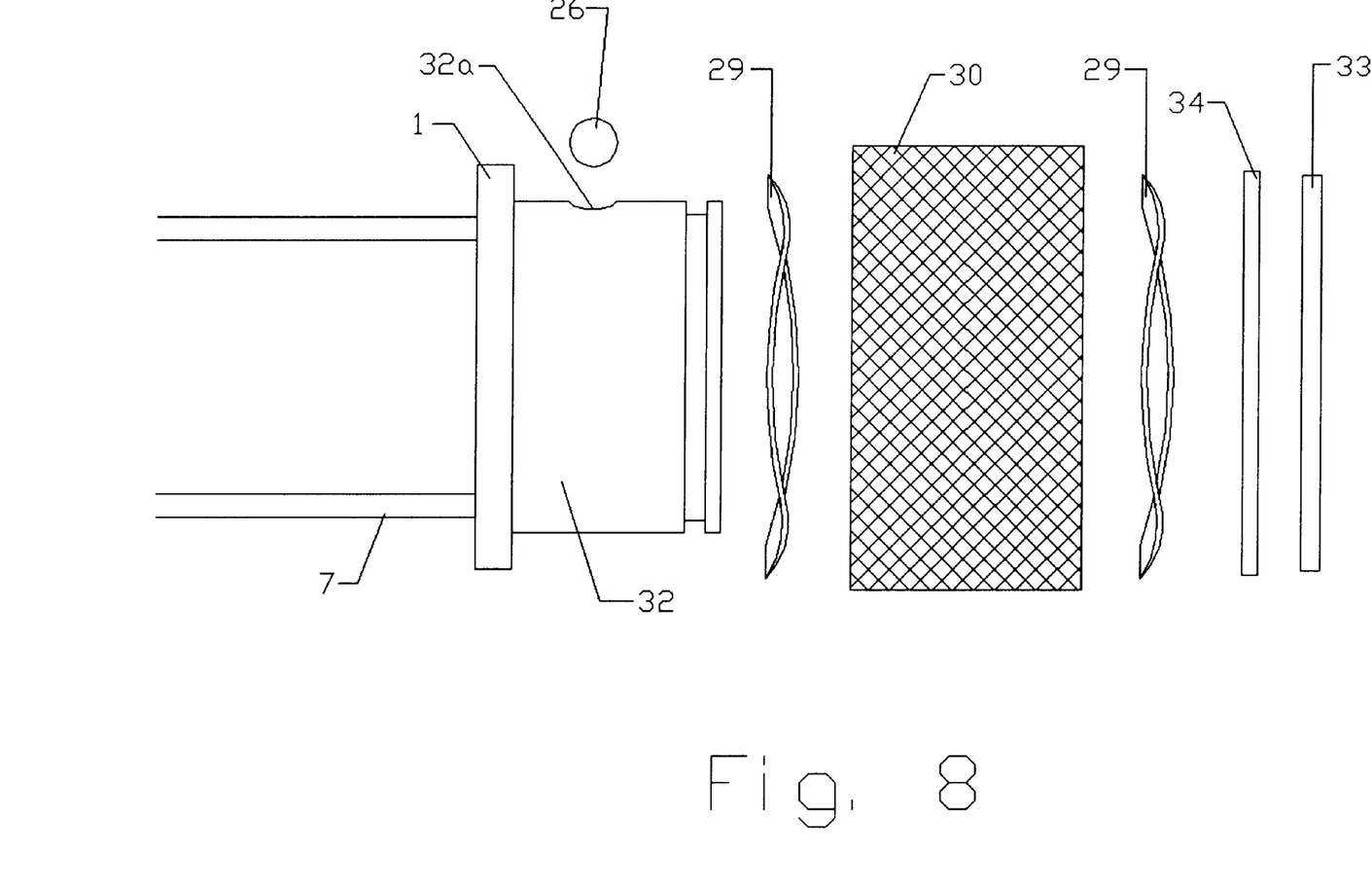
FIG. 8 shows an exploded detailed plan view of the ball mechanism used in FIG. 6.
Figure 8A:
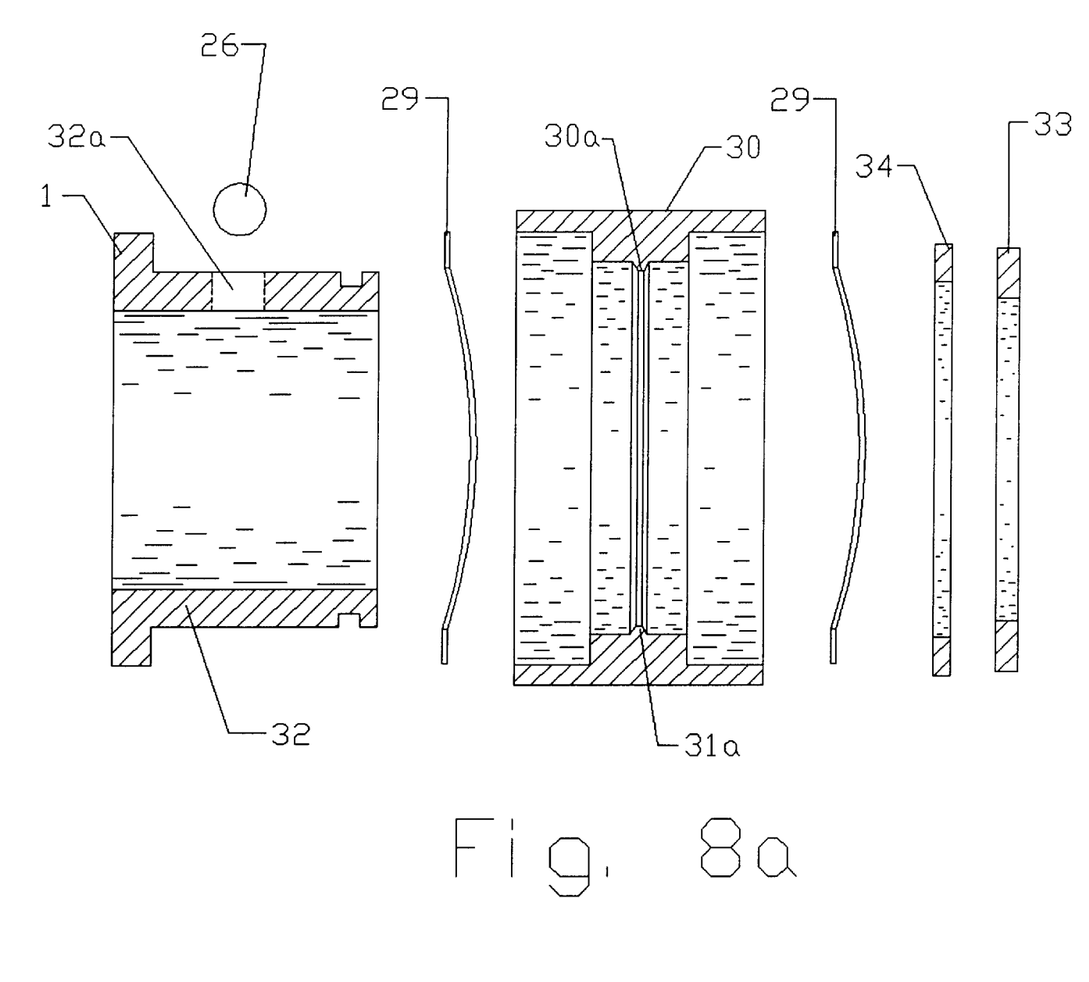
FIG. 8a shows a cross sectional view of FIG. 8.
Figures 9A, 9B:
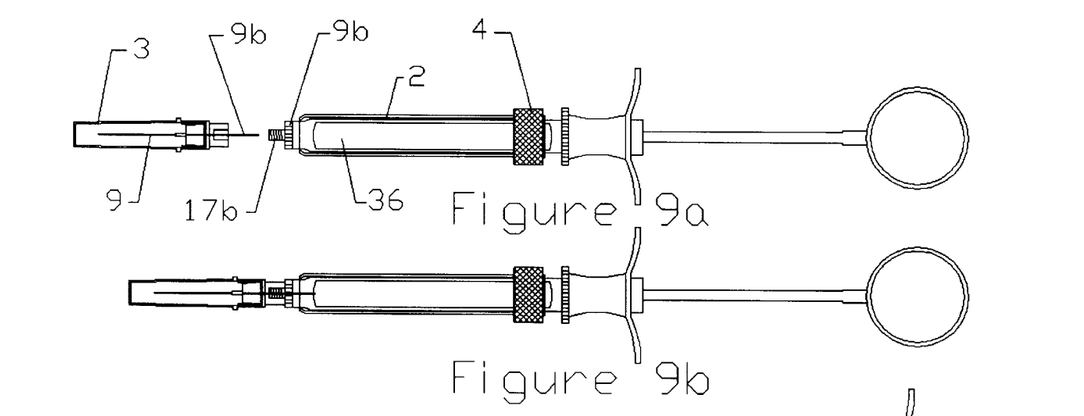
Figure 9C:
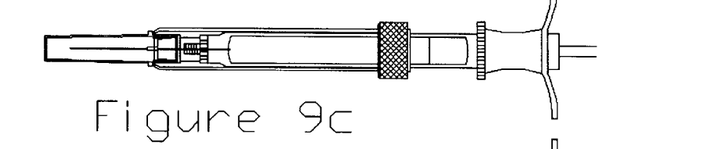
Figure 9D:
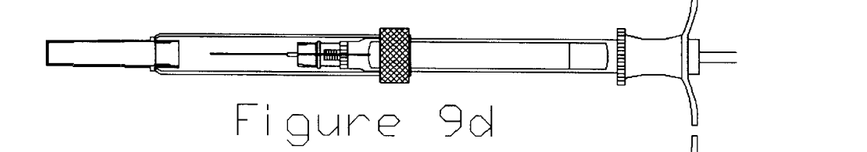
Figure 9E:
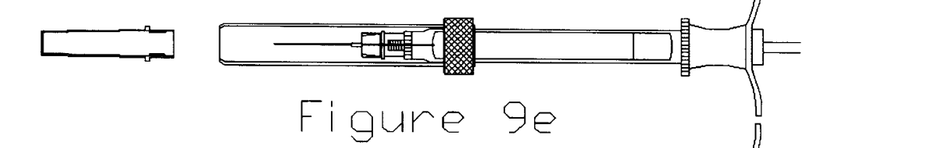
Figure 9F:
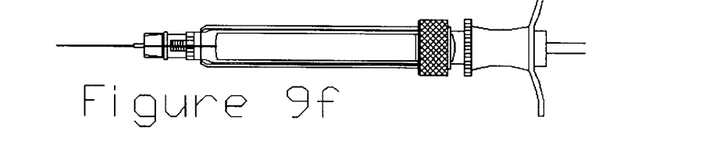

FIGS. 8 in plan view and 8a in cross sectional view and 10 shows the ball in groove (dips 37a and 37b) mechanism for practicing this invention. This mechanism involves a ball 26 held by the action of springs 29 on the inside of element 31 allowing the ball to fall within a hole 32a in the ball holder 32. The mechanism is held together by pressure of a bolt or snap ring 33 on washer 34. Housing 30 fits over the ball holder 32 to prevent the the ball from coming out. A raised point 30a on housing 30 pushes the ball 26 within the dip 37. As shown in FIG. 6b, the ball 26 can come out of the dip 37 by pushing against one of the springs 2 until the ball rolls over the dip 37 at which time it will fall back within the dip 37 and be releasably held therein by the point 30a as shown in FIG. 6a.

Figure 7:
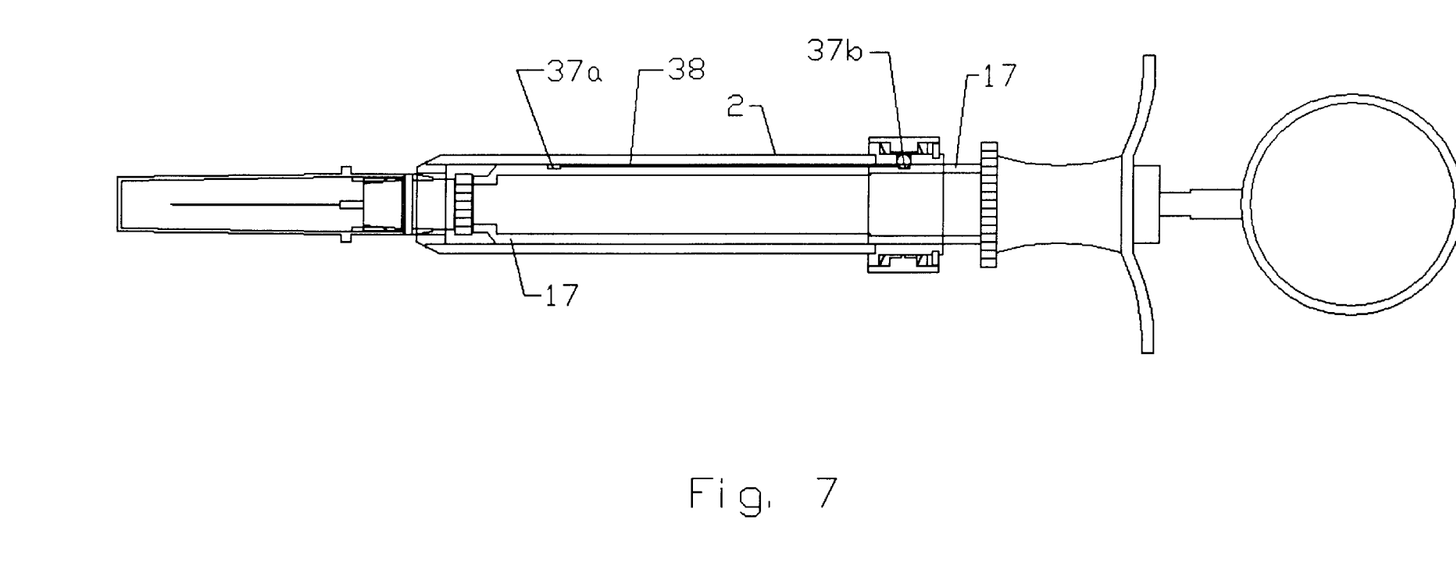
FIG. 7 is a cross sectional view of the embodiment detailed in FIG. 6.

Referring to FIG. 9, the process by which the present invention is used can be described in the following steps. The needle with the cap in place is attached to the syringe 17 at the screw 17b as Shown in FIG. 9a. At this point, as shown in FIG. 7, the ball 26 holds the cover 2 in the rearward dip 37b. The rear 9b of the needle 9 pierces a carpule (not shown) in the opening in the syringe 36 provided for this purpose. The unit of the needle, cap and syringe may be handled safely as shown in FIG. 9b.

At this point, the locking mechanism 35 is released by moving the lock sleeve 31 forward or back against the forward or rear spring 39, moving the notch 31a off of the ball 26 which allows the ball 26 to leave the dip 38b and allows the ball 26 to travel easily in a groove 38 in the syringe running between the two dips 37a and 37b as shown in FIG. 7 to keep the cover alligned where desirable. As shown in FIG. 9c, the cover 2 is slid forward until in grips the needle cap. The needle cap may be held on by the user to insure it does not pop off prematurely. Next, the cover is pushed farther forward as shown in FIG. 9d so that the needle 9 is protected by the cover and the cap may be completly removed as shown in FIG. 9e. At this point in time, as shown in FIG. 7, the ball 26 is, by action of the springs 29 held against the raised notch 31a and within hole 32a into the forward dip 37a. The travel of the lock sleeve 31 may be fixed in place to prevent the ball 26 from coming out of the dip 38a in the syringe.

Figure 10C:
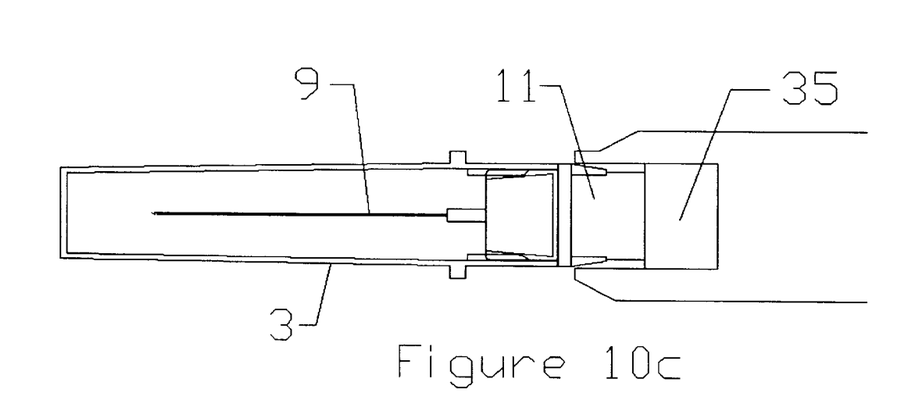

The cap 3 may be removed at this point in time as shown in FIG. 9e so that the needle 9 is protected only by the cover 2. When the needle 9 is to be used, the cover 2 is moved to the rear portion of the syringe exposing the needle 9 as shown in FIG. 9f. The cover is extended back over the needle 9 when the use is finished. Replacing the cap is merely a reversal of this process. In the alternative embodiment shown in FIGS. 10a–c, rather than unscrewing the needle and cap, they are broken off through the opening 25 in the syringe. A plate 25 may seal the opening 25 as shown in FIGS. 10c, cover closed, and 10c, cover open. As shown in 9f, the cover comes back far enough to allow the needle to snap off without having a cut out of the cover.

In the preferred embodiment, when the user is finished the needle cover is extended so that it fully covers the needle and there is no chance of being stuck with the needle and may lock in place in this position for added safety. A locking means may be provided such as a turning lock when the hypodermic cover is fully extended. At this point in time the needle cover may be snapped in place in the preferred embodiment onto the hypodermic cover the device is designed so that the needle cover remains in place on the hypodermic cover until the hypodermic cover pulls the needle cover firmly back in place on the needle holder. At this point in time the needle cover may be removed and disposed of with a greatly reduced chance of potential contamination or sticking of the user.

The invention may also be described by way of a process for utilizing a syringe receiving a needle holder having a cap the steps of:
1. Sliding a cover over the end of the syringe receiving the needle holder.
2. Inserting the needle holder within the cover so that the needle cap is held by contact with the needle cover.
3. Moving the assembly of the needle cover, cap and needle holder back so that the needle holder may be joined to the syringe.

The process may be further described in terms defining the replacement of the cap as follows:
1. Sliding the needle holder over a needle held on a syringe.
2. Attaching the needle cap to the needle cover.
3. Drawing the needle cap and cover assembly back over the needle holder as the cap is placed back on the needle while the cap and needle cover protect the user from the needle.

Because many varying and different embodiments may be made within the scope of the inventive concept herein taught and because many modifications may be made in the embodiment(s) herein detailed in accordance with the descriptive requirements of the law, it is to be understood that the details herein are to be interpreted as illustrative and not in a limiting sense.

We claim:

1. A device for protecting a needle said needle being held by a hub, said needle hub being attachable to a syringe having an axis, said needle hub also capable of receiving a needle cap, said needle cap having a length and a front portion and a rear portion, said rear portion defining a rear portion outer diameter and a raised wall having an outer diameter attached to the front needle cap between the front portion, the rear portion and said cap further defining an interior for receiving the needle interior to the cap, said device comprising:

(A) a cover means for covering the needle said cover means having a front end and a bottom end said cover means being slidable over the syringe axis, said cover means comprising a reduced end on the front end, said reduced end defining a reduced end opening and a reduced end inner length said reduced end having an inner diameter and which reduced end inner diameter is less than the raised wall outer diameter and wherein the reduced end inner diameter is approximately the same as the cap rear portion outer diameter so that the cap rear portion outer diameter is frictionally held by the reduced end inner length when the reduced end inner length is slid over the cap rear portion and where when the reduced end is pushed against the raised wall, the reduced end pushes the needle cap away from and off of the needle hub.

2. The device of claim 1 wherein the reduced end inner length is made of elastic material.

3. The device of claim 1 wherein said cap rear portion is made of elastic material.

4. The device of claim 3 wherein said cap rear portion has the same shape as the reduced end inner length.

5. The device of claim 1 wherein the reduced end further comprises a gripping means for securely holding the cap rear portion.

6. The device of claim 5 wherein the gripping means further comprises at least one slot defined by said cover reduced end to allow said cover reduced end to expand as the cover reduced end is slid over the cap rear portion.

7. The device of claim 5 wherein said gripping means comprises an elastic washer mounted onto the cover reduced end having a uncompressed washer diameter less than the cup rear portion.

8. The device of claim 1 wherein the cover means further comprises a body continuous with the reduced end and said body having a cover diameter wherein said cover diameter is greater than said syringe, so as to be slidable over the syringe.

9. The device of claim 8 wherein the body further comprises an a protected length having an exterior surface and wherein the cover means further comprises an air passage restriction means for separating the reduced end from the protected length exterior surface of the body so as to restrict the flow of air between the reduced end and the protected length so as to prevent the protected length from fogging up.

10. The device of claim 9 wherein the air passage restriction means further comprises an o-ring seal on the syringe barrel between the reduced end and the protected length.

11. The device of claim 1 wherein the syringe further comprises a barrel, said barrel having a barrel length and wherein the cover further comprises an internal ridge running parallel with the barrel and between the barrel and the cover so as to hold the cover above the syringe to prevent scratching as the cover moves over the syringe barrel.

12. A device for protecting a needle having a cap, said cap having a rear diameter, when said needle is in place on a syringe, said syringe having a barrel, said barrel defining a barrel outer surface having a forward surface and a rear surface and said syringe having an axis passing from the forward surface to the rear surface comprising:

(A) a cover means for covering the needle, said cover means having a bottom end slidable from the rear surface to the forward surface over the same axis as the syringe and over the needle and wherein the syringe further comprises at least one lock point on the outer surface and wherein the cover means further comprises a first locking means for fixing the position of the cover relative to the at least one lock point; and (B) wherein the syringe further comprises a second lock point and wherein the locking means further comprises a second locking means so that the cover means may be secured substantially over the rear surface exposing the needle.

13. The device of claim 12 wherein the locking means further comprises a ball means for rolling over the barrel on the cover said first locking means further comprising a biasing means attached to the cover for pushing on the ball means in contact with the syringe barrel and wherein the barrel defines at least one first dip on the syringe at the first lock point for receiving a portion of the ball means.

14. The device of claim 13 wherein the syringe further comprises a second lock point and wherein the barrel further comprises a second dip at the second lock point so that the cover may be secured at the first lock point to cover the needle and at the second lock point at the second dip so as to leave the needle exposed.

* * * * *